United States Patent [19]
Aggarwal et al.

[11] Patent Number: 5,824,636
[45] Date of Patent: Oct. 20, 1998

[54] ANTIPROLIFERATIVE PROTEIN FROM *BACILLUS THURINGIENSIS* VAR. *THURINGIENSIS*

[75] Inventors: Bharat B. Aggarwal, Houston, Tex.; Cristina Rodriguez-Padilla, Monterrey, Mexico

[73] Assignees: Research Development Corporation, Carson City, Nev.; Universidad Autonoma de Nuevo Leon, Nuevo Leon, Mexico

[21] Appl. No.: 743,553

[22] Filed: Nov. 4, 1996

Related U.S. Application Data

[63] Continuation of Ser. No. 454,636, May 31, 1995, abandoned.

[51] Int. Cl.$^6$ ............ A61K 39/07; A61K 38/16; C07K 14/32
[52] U.S. Cl. .................. 514/2; 530/350
[58] Field of Search ............... 530/350; 514/2; 424/93.461

*Primary Examiner*—Keith D. Hendricks
*Attorney, Agent, or Firm*—Benjamin Aaron Adler

[57] ABSTRACT

The present invention provides an isolated and purified protein derived from *Bacillus thuringiensis* subspecies thuringiensis, having a molecular weight of approximately 20 kDa of SDS-PAGE, said protein having the partial amino acid sequence shown in SEQ ID No. 1, and wherein said protein displays cytotoxic effects against tumor cells. Also provided is a method of treating a neoplastic cell comprising administering a therapeutically effective dose of the composition of the present invention to said cell.

11 Claims, 19 Drawing Sheets

```
         1                    5                         10
NH2 -Pro-Ser-Thr-Val-Val-Asn-Val-Ser-Asn-Leu- 15                         20
    -Lys-Pro-Gly-Asp-Thr-Ile-Glu-Lys-(Glu)-Phe-
```

ANTIPROLIFERATIVE PROTEIN FROM *BACILLUS THURINGIENSIS* VAR. *THURINGIENSIS*

CROSS-REFERENCE TO RELATED APPLICATION

This application is a Continuation of the Non-Provisional patent application which claims benefit of U.S. Ser. No. 08/454,636 that was filed on May 31, 1995.

BACKGROUND OF THE INVENTION

1. Field of the Invention

The present invention relates generally to the fields of immunology and protein chemistry. More specifically, the present invention relates to the isolation, purification and characterization of a novel antiproliferative protein from *Bacillus thuringiensis* var.thuringiensis.

2. Description of the Related Art

Agents that display antiproliferative properties selectively against tumor cells have potential as anticancer drugs. These types of agents have been sought from both synthetic as well as natural sources. Such compounds with antiproliferative properties could be either proteinaceous or nonproteinaceous in nature.

Both gram-negative and gram-positive bacteria are known to synthesize proteins that are toxic to eukaryotic cells. *Bacillus thuringiensis* is a gram positive bacteria that during sporulation synthesizes large quantities of a protein that when ingested can kill insects (Hofte and Whiteley, 1989). This protein has been used as a microbial pesticide for more than 30 years, and it is considered harmless to humans (Green et al, 1990). These insecticidal proteins are assembled in the bacteria as crystalline parasporal bodies and fall into three different size classes, 133–145 kDa; 65–67 kDa and 27 kDa. Different subspecies of *Bacillus thuringiensis* may express one or more of each size classes. The 133–145 kDa protein is a protoxin which when degraded by mid-gastrointestinal proteases yields an amino terminal fragment of about 67 kDa that contains the toxin moiety (Ogiwara etal, 1992). The 67 kDa toxin shares a significant structural homology with toxins from various other subspecies of *Bacillus thuringiensis*. The 27 kDa toxin, however, shows no homology with any of the other size classes of toxins but is highly homologous within the subspecies (Luthy et al., 1982). The gene for 27 kDa toxin from subspecies israeliensis (*Bacillus thuringiensis* israeliensis), kyushunsis (*Bacillus thuringiensis* kursataki) and morrisoni (*Bacillus thuringiensis* morrisoni) have been cloned and found that the *Bacillus thuringiensis* israeliensis toxin differs by a single base from *Bacillus thuringiensis* morrisoni toxin; whereas it is only 39% identical to *Bacillus thuringiensis* kursataki toxin (Waalwijk et al., 1985; Ward and Ellar, 1986; Ward et al., 1986; Galjart et al., 1987; Koni and Ellar, 1993). The toxins from various subspecies have been shown to be cytolytic to insect cells in culture.

Almost 20 years ago, it was reported that a toxin derived from *Bacillus thuringiensis* subspecies thuringiensis has antitumor activity against certain murine tumors such as Yoshida ascites sarcoma in vivo. Subsequently, it was shown that a toxin derived from *Bacillus thuringiensis* israeliensis also has antitumor activity against certain type of murine tumor cells in vitro. The *Bacillus thuringiensis* thuringiensis protein enhances the humoral immune system in rats and guinea pigs, and induces long lasting antitumor immunity as judged by the rejection of the subsequent tumor transplant. The structural characterstics of this antitumor protein and whether it is functionally related to the insecticidal toxins described above from various other subspecies, is not known.

The prior art is deficient in the lack of effective means of inhibiting the growth of a wide variety of tumors. The present invention fulfills this longstanding need and desire in the art.

SUMMARY OF THE INVENTION

The present invention describes the isolation and characterization of a protein, named oncotoxin, from a gram positive bacteria *Bacillus thuringiensis* var. thuringiensis. The identification of oncotoxin was based, in part, on its antiproliferative activity against human histiocytic lymphoma U-937 cells. By using this assay, oncotoxin was isolated by a differential sodium bromide gradient ultracentrifugation, proteolytic digestion followed by DEAE affigel blue affinity chromatography. The oncotoxin activity bound to DEAE affigel blue resin and could be eluted with 0.05M NaCl. It has an approximate molecular mass of 20 kDa under denaturing conditions.

The biological activity of the purified protein was sensitive to various proteolytic enzymes including trypsin, chymotrypsin and pronase, sensitive to acidic conditions (pH below 4), sensitive to triflouroacetic acid (0.1%) and to acetonitrile (50%). Oncotoxin activity, however, was resistant to elevated temperatures (30 minutes at 100° C.) and to reducing conditions (1 mM dithiothreiotol). The amino terminal amino acid sequence of this protein consisted of NH2-Pro-Ser-Thr-Val-Val-Asn-Val-Ser-Asn-Leu-Lys-Pro-Gly-Asp-Thr-Ile-Glu-Lys-Glu-Phe-. This sequence was unique when compared to published sequences of other proteins. A synthetic peptide based on this sequence was used to prepare polyclonal antibodies in rabbits, and these antibodies completely neutralized the biological activity of oncotoxin even at 1:10,000 dilution of the antiserum. Western blot analysis with these antibodies also revealed a band of oncotoxin at 20 kDa.

Besides thymidine incorporation method, trypan blue exclusion and MTT methods also showed a complete inhibition of the long-term growth of U-937 cells by a highly purified oncotoxin. The latter displayed antiproliferative effects against a wide variety of different tumor cell lines including myeloid (U-937, THP-1, HL-60), lymphoid (Raji, Jurkat), erythroblastoid (K-562), breast carcinoma (CLO, MCF-7), ovarian carcinoma (OVCA429, OVCA 432, OVCA 433), kidney (A-293) and hepatoma (Hep3B, HepG2). Under similar conditions, human glioblastoma (U-251) and murine fibrosarcoma (L-929) were, however, resistant to oncotoxin. Normal human diploid foreskin fibroblast and normal human peripheral blood lymphocytes were also resistant to Oncotoxin even up to 100 µg/ml concentration. The treatment of U-937 cells with oncotoxin for 24 hours lead to DNA fragmentation as monitored by an agarose gel electrophoresis suggesting that the mechanism of cell death by oncotoxin is most likely through apoptosis. Overall, the present invention demonstrates the isolation of a novel bacterial protein that has antiproliferative effects against wide variety of tumor cells.

In one embodiment of the present invention, there is provided a composition of matter comprising an isolated and purified protein derived from *Bacillus thuringiensis* subspecies thuringiensis having a molecular weight of approximately 20 kDa by SDS-PAGE, said protein having the partial amino acid sequence shown in SEQ ID No. 1, and wherein said protein displays cytotoxic effects against tumor cells.

In another embodiment of the present invention, there is provided a pharmaceutical composition, comprising the novel protein of the present invention and a pharmaceutically acceptable carrier.

In yet another embodiment of the present invention, there is provided a method of preparing the protein of the present invention. In still yet another embodiment of the present invention, there is provided a method of treating a neoplastic cell comprising administering a therapeutically effective dose of the composition of the present invention to said cell.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows the amino terminal amino acid sequence analysis of oncotoxin.

DETAILED DESCRIPTION OF THE INVENTION

Figure 1:
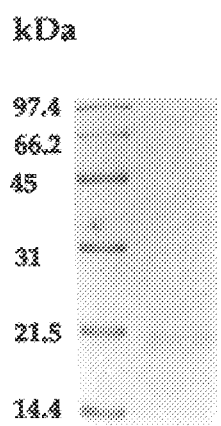
FIG. 1 shows the sodium dodecyl sulfate polyacrylamide gel analysis of oncotoxin. One μg of oncotoxin was resolved on 15% acrylamide gels as described below.

The present invention is directed to a composition of matter comprising an isolated and purified protein derived from *Bacillus thuringiensis* subspecies thuringiensis, having a molecular weight of approximately 20 kDa of SDS-PAGE, said protein having the partial amino acid sequence shown in SEQ ID No. 1, and wherein said protein displays cytotoxic effects against tumor cells. As described completely below, this novel protein is sensitive to proteases and acidic conditions and the cytotoxic effects are resistant to treatment with dithiothreiotol or exposure to 100° C. temperature.

Although the novel protein of the present invention may be cytotoxic to a very wide variety of tumor cells, it is generally cytotoxic to U-937 cells, myeloid cells, B lymphoid cells, T lymphoid cells, erythroblastoid cells, breast tumor cells, ovarian tumor cells and hepatoma cells. The protein is not cytotoxic to normal human cells, such as peripheral blood lymphocytes and human foreskin fibroblast cells. The cytotoxic effects are blocked by an antibody directed against the protein.

It is specifically contemplated that pharmaceutical compositions may be prepared using the novel protein of the present invention. In such a case, the pharmaceutical composition comprises the novel protein of the present invention and a pharmaceutically acceptable carrier. A person having ordinary skill in this art would readily be able to determine, without undue experimentation, the appropriate dosages and routes of administration of the novel protein of the present invention. When used in vivo for therapy, the protein of the present invention is administered to the patient or an animal in therapeutically effective amounts, i.e., amounts that eliminate or reduce the tumor burden. It will normally b e administered parenterally, preferably intravenously, but other routes of administration will be used as appropriate. The dose and dosage regimen will depend upon the nature of the cancer (primary or metastatic) and its population, the characteristics of the particular immunotoxin, e.g., its therapeutic index, the patient, the patient's history and other factors. The amount of protein administered will typically be in the range of about 0.1 to about 10 mg/kg of patient weight. The schedule will be continued to optimize effectiveness while balanced against negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press; which are incorporated herein by reference.

For parenteral administration the protein will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The immunotoxin will typically be formulated in such vehicles a t concentrations of about 0.1 mg ml to 10 mg ml.

The level of ordinary skill of the average scientist in the area of molecular biology has increased substantially in recent years. A person having ordinary skill in this art would readily be able to clone the gene for this novel cytotoxic protein given the teachings of the present specification.

The present invention is also directed to a method of treating a neoplastic cell comprising administering a therapeutically effective dose of the composition of the present invention to said cell. Preferably, the neoplastic cell is selected from the group consisting of myeloid cells, B lymphoid cells, T lymphoid cells, erythroblastoid cells, breast tumor cells, ovarian tumor cells and hepatoma cells. Generally, the neoplastic cell may be in a human or animal. It is specifically contemplated that the novel composition will retard recurrence of a neoplastic condition and extend the survival time of a host of said neoplastic cell.

The protein of the present invention may also be used in an in vitro method. For example, the method may be used in killing tumor cells from bone marrow. In this method, the bone marrow is first removed from an individual having a neoplastic disease. Subsequently, the bone marrow is treated with a cytocidally effective dose of an protein of the present invention to eliminate the residual tumor cells. The treated bone marrow cells can be re-administered to the patient to facilitate re-establishment of an immune system after receiving intensive chemotherapy and/or radiotherapy to eliminate all endogenous neoplastic hemotoxic cells.

The following examples are given for the purpose of illustrating various embodiments of the invention and are not meant to limit the present invention in any fashion. cl EXAMPLE 1

Materials

RPMI-1640 was obtained from Whittaker MA Bioproducts (Walkersville, Md.). Fetal bovine serum (FBS) and gentamicin were from GIBCO (Grand Island, N.Y.). Other chemicals and biochemicals were obtained from Sigma Chemical Co. (St Louis, Mo.). U-937 (histiocytic lymphoma, CRL 1593), promyelocytic leukemia HL-60 (CCL 240); acute myelogenous leukemia KG-1a (CCL 246.1); breast adenocarcinoma MCF-7 (HTB 22); epidermal carcinoma HepG-2 (CCL 23); breast carcinoma BT-20 (HTB 19); Burkitt's lymphoma Raji (CCL 86); and Jurkat (acute T cell leukemia, TIB 152) cell lines were obtained from the American Type Cell Culture Collection (Rockville, Md.). Cells were routinely grown in RPMI 1640 medium supplemented with glutamine (2 mM), gentamicin (50 mg/ml), and fetal bovine serum (10%). *Bacillus thuringiensis* kurstaki toxin made by recombiant DNA method (called Cry IIA) (Donovan etal, 1988) was supplied by Dr. William P. Donovan of Ecogen Inc. (Langhorne, Pa.).

EXAMPLE 2

Oncotoxin Bioassay

The biological activity of oncotoxin was monitored by its ability to inhibit thymidine incorporation in human histiocytic lymphoma U-937 cells during the 72 hour time period. This assay was carried out as previously described (Higuchi and Aggarwal, 1992). Briefly, cells ($5 \times 10^3$ /0.1 ml) were plated in 96-well Falcon plates. Serial dilutions of oncotoxin were added to the target cells and incubated for 72 hours at 37° C. During the last 6 hours of the 72 hour incubation, tritiated thymidine (6.7 Ci/mmole; New England Nuclear, Boston, Mass.) was added to each well (0.5 mCi/well). The cell suspension was then harvested with the aid of a Packard Filtermate 196 cell harvester onto a glass fiber filter, and radioactivity bound to the filter was measured in a Packard Matrix 9600 direct beta counter (Packard Co., Meriden, Conn.). Relative cell viability was calculated as the amount incorporated in treated cells divided by that in the untreated cells and expressed as a percentage.

The growth of U-937 cells was measured by the modified tetrazolium salt (MTT) assay (Hansen etal, 1989). Briefly, cells (5000 cells/well) were incubated in the presence or absence of different concentrations of oncotoxin in a final volume of 0.1 ml for different days at 37° C. Thereafter, 0.025 ml of MTT solution (5 mg/ml in PBS) was added to each well. After a 2 hour incubation at 37° C., 0.1 ml of the extraction buffer (20% sodium dodecyl sulfate, 50% dimethyl formamide) was added. After an overnight incubation at 37° C., the optical densities at 570 nm were measured using a 96-well multiscanner autoreader (Dynatech MR 5000), with the extraction buffer as a blank.

EXAMPLE 3

Microorganism and growth conditions

*Bacillus thuringiensis* var. thuringiensis was obtained from Immunology and Virology Laboratory, Faculty of Biological Sciences, Autónoma University of Nuevo León. The bacteria was maintained on a nutrient agar slant at 4° C. and subcultured every three months as described (Cheung and Hammock, 1985).

EXAMPLE 4

Production of crystals and spores

The production of crystals and spores was carried as described previously (Yamamoto and McLaughlin, 1981; Yamamoto and Ilzuka, 1983). Briefly, bacteria was cultivated in nutrient broth for 18 hours at 30° C. with constant shaking. A sample of this culture was used to inoculate agar medium culture flask for 72 hours at 30° C. and then crystals were harvested in 1M NaCl by centrifugation (Beckman) at 10, 000 rpm for 30 minutes at 4° C. The pellet was washed three times in 1M NaCl, and stored at −20° C.

EXAMPLE 5

Isolation of protein crystal

The crystals were separated from the spores by differential ultracentrifugation, using sodium bromide gradients (30, 31.5, 33, 34.5 and 36%) at 25 000 rpm (Beckman centrifuge L5-50E, rotor SW-2T) for 90 minutes at 4° C. Bands containing the crystals were pooled, washed three times with deionized water, lyophilized and stored at −20° C. (Ang and Nickerson, 1978).

EXAMPLE 6

Solubilization of crystals

This step was carried out as described by Prasad and Shethna, 1974. Briefly, 100 mg crystal protein was suspended in 20 ml of 1M NaOH in 0.1M glycine for 5 hours at room temperature and then centrifuged (20,000 rpm for 30 minutes at 4° C.). The supernatant referred to as alkali-solubilized crystals, was dialyzed against phosphate buffered saline pH 7.2. The sample was lyophilized and stored at −20° C .

EXAMPLE 7
Activation of alkali-solubilized crystals by trypsin

The procedure of Choma et al. (1990) was adopted for this step. Briefly, alkali-soluble fractions (5 mg/ml) were treated with trypsin (10%; W/W) in 0.1M glycine buffer pH 7.2 for 30 minutes at 37° C. The sample was centrifuged at 20,000 rpm (Beckman centrifuge) for 30 minutes at 4° C., and then the supernatant was dialyzed against phosphate buffered saline pH 7.2.

EXAMPLE 8
DEAE-Affigel blue affinity chromatography

An oncotoxin fraction (approximately 2 mg/ml) obtained from the above step was applied to DEAE-Affigel blue column (1 X 6.5 cm) pre-equilibrated in 20 mM Tris, pH 8. The column was washed with the equilibration buffer and then eluted with a step-up gradients of 0.05–1.0M NaCl. Oncotoxin fractions were identified by bioassays and the protein concentration was measured by the Biorad method.

EXAMPLE 9
DNA fragmentation analysis

Cells ($5\times10^6$/ml) were treated with oncotoxin (50 ug/ml) for 24 hours or 72 hours and then spun down, washed with PBS, and resuspended in 10 mM tris-Cl, pH 7.4 and 1 mM EDTA, pH 8. Then the cells were lysed with lysis buffer (10 mM tris-Cl pH 8, 100 mM NaCl, 25 mM EDTA, and 0.5% SDS), and RNA removed by adding RNase (1 $\mu$l of 10 mg/ml). After incubation at 50° C. for 30 minutes, 1 $\mu$l of proteinase K (20 mg/ml) was added to all the tubes and incubation continued for another 30 minutes at 50° C. After adding 0. 4 $\mu$l of loading dye (0.025% bromophenol Blue, 0.25% xylene cyanol FF, and 30% glycerol in water), the samples were resolved on 1.2% agarose gel in TAE buffer (0.04M Tris-acetate, 0.001M EDTA).

EXAMPLE 10
Amino acid sequence analysis

The amino acid sequence of oncotoxin was carried out by a Protein sequencing facility at Baylor College of Medicine (Houston, Tex.). From SDS-PAGE gels the protein was transfered on to PVDF membranes and then subjected to sequence analysis on microsequencer model 473A (Applied Biosystems Inc., Foster City, Calif.). The sequence homology searches were performed at the National Center for Biotechnology Information (NCBI) using the BLAST network service.

EXAMPLE 11
Peptide Synthesis

Based on amino acid sequence of oncotoxin, an 18 amino acid long peptide was synthesized by the Protein chemistry core facility of the Baylor College of Medicine (Houston, Tex.). Fmoc multiple antigenic peptide (MAP) resins were used for the synthesis of the oncotoxin peptide. The synthetic peptide was purified by reverse phase HPLC and characterized for amino acid composition.

EXAMPLE 12
Antibody Production

The peptide as synthesized above was used to make antibodies (Bethyl Laboratories, Montgomery, Tex.) by immunizing rabbits subcutaneously (multiple sites) with 100 $\mu$g of the antigen in complete Freunds adjuvant. This was followed by two intramuscular injections of 50 $\mu$g each in an incomplete Freunds adjuvant on day 14 and day 21. Thereafter, the serum was tested for neutralization titers in the oncotoxin bioassay and for the immuno-reactivity by the western blot analysis.

EXAMPLE 13
Western Blot Analysis

The protein samples were electrophoresed on an SDS-polyacrylamide gel (15%). After electrophoresis samples were transferred to nitrocellulose filter paper in a buffer containing Tris-HCl (25 mM, pH 8.3), glycine (192 mM), and methanol (20%, v/v). The nonspecific binding on the nitrocellulose filter paper was minimized with a blocking buffer containing BSA (5%) and Tween 20 (0.1%, v/v) in PBS (PBS-tween buffer) for 1 hour at room temperature. After three washes with PBS-Tween buffer, filter paper was incubated with anti-oncotoxin antibody (1:10,000 dilution) for 1 hour at room temperature. The filter paper was washed again and then incubated with goat anti-rabbit IgG-horseradish peroxidase conjugate (1:10000 dilution) for 1 hour at room temperature. Thereafter, the filter paper was washed four times, and bands were visualized with the enhanced chemiluminescence system (Amersham).

EXAMPLE 14
Isolation and Physicochemical Characterization of Oncotoxin

By using the U-937 cytotoxicity bioassay and the purification protocol consisting of gradient ultracentrifugation, proteolytic activation and DEAE affigel blue affinity chrmatography, a protein was isolated that eluted from DEAE at 0.05M NaCl. This protein, is refered herein as oncotoxin. Analysis under denaturing conditions by SDS-PAGE revealed, both by coomassie blue and by silver staining, one major band at an approximate molecular mass of 20 kDa (FIG. 1). Oncotoxin was electroblotted onto a PVDF membrane and then amino acid sequence analysis was carried out. The amino terminal sequence obtained is shown in FIG. 2. When examined using both peptide and nucleotide sequence data base, it was found that the sequence of oncotoxin is novel.

Figure 3:
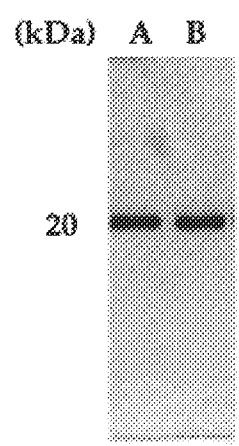
FIG. 3A shows the detection of oncotoxin by western blot analysis.
FIG. 3B shows the neutralization of the biological activity of oncotoxin by antibodies against the synthetic oncotoxin peptide.
Figure 4:
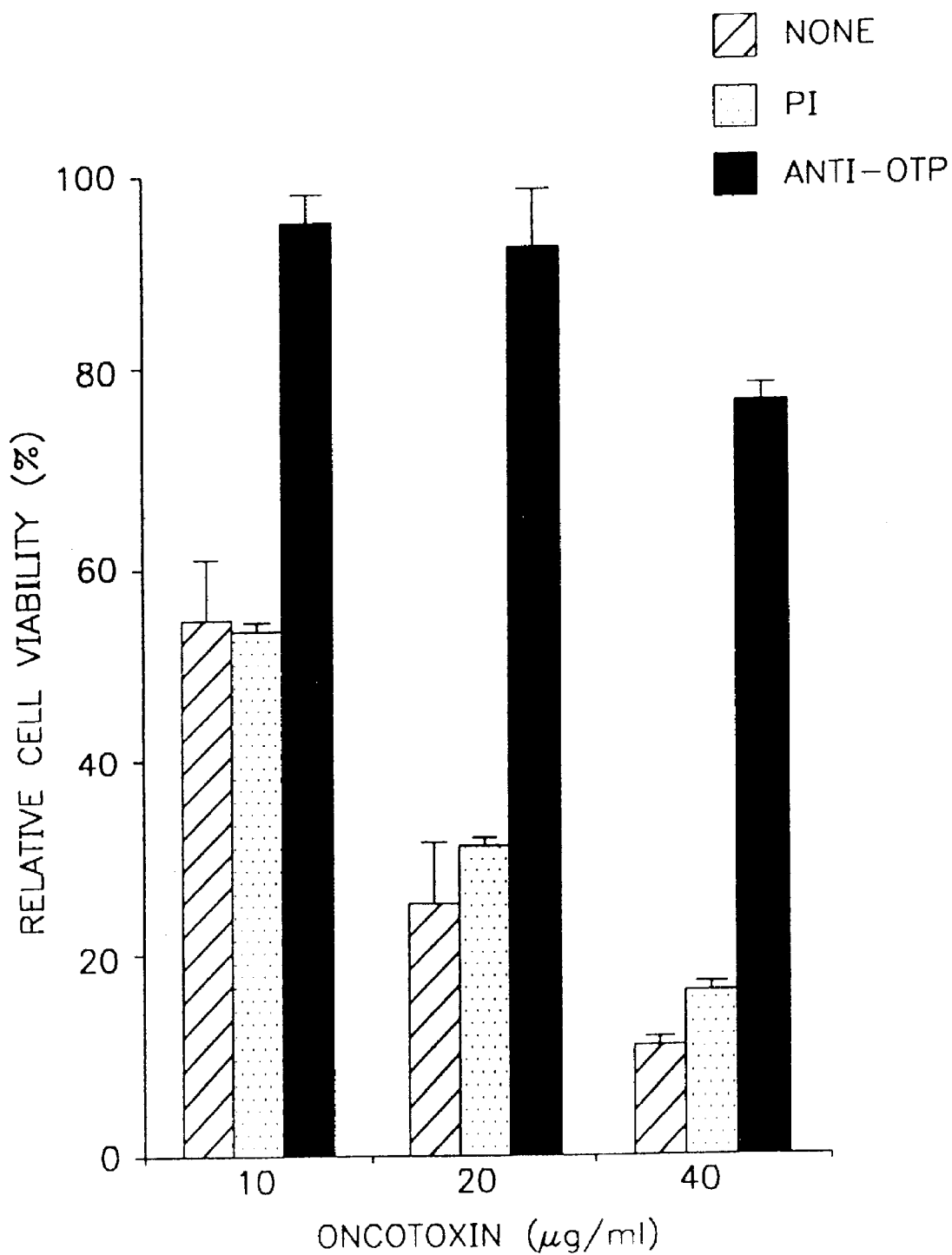
FIG. 4 shows the comparison of the effects of oncotoxin with a synthetic peptide based on its amino acid sequence.

Based on this sequence, the peptide was synthesized and this peptide was then used to immunize rabbits. The antibodies obtained against the oncotoxin peptide cross reacted with the oncotoxin protein on western blot analysis (FIG. 3A). This antibody was also able to neutralize the biological activity of oncotoxin even at 1 to 10, 000 dilution of the antisera (FIG. 3B). Although much less than the full-length protein, the synthetic oncotoxin peptide had some activity against U-937 cells (FIG. 4).

Figure 5:
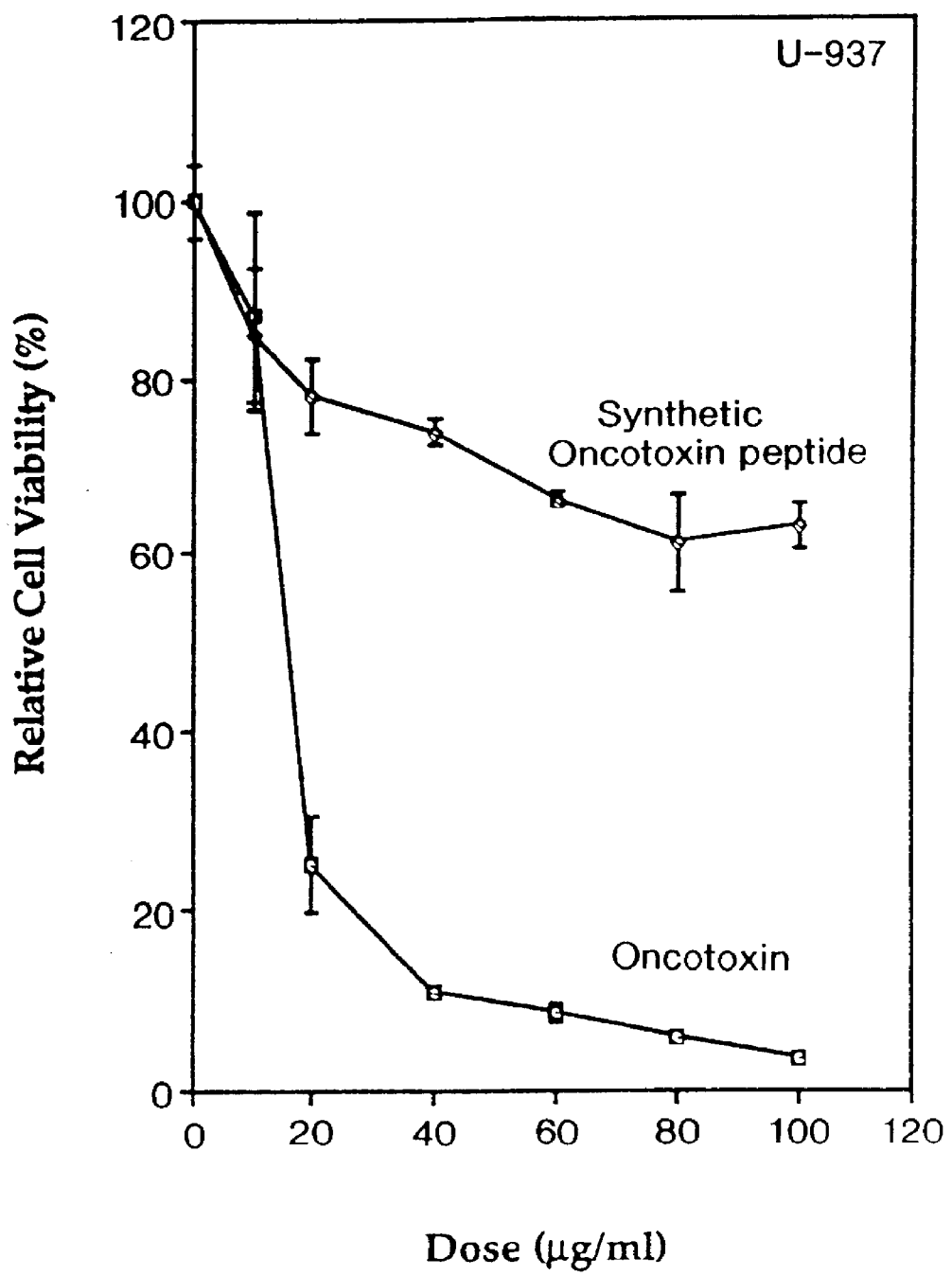
FIG. 5 shows the effect of various peoteases on the biological activity of oncotoxin.
Figure 6:
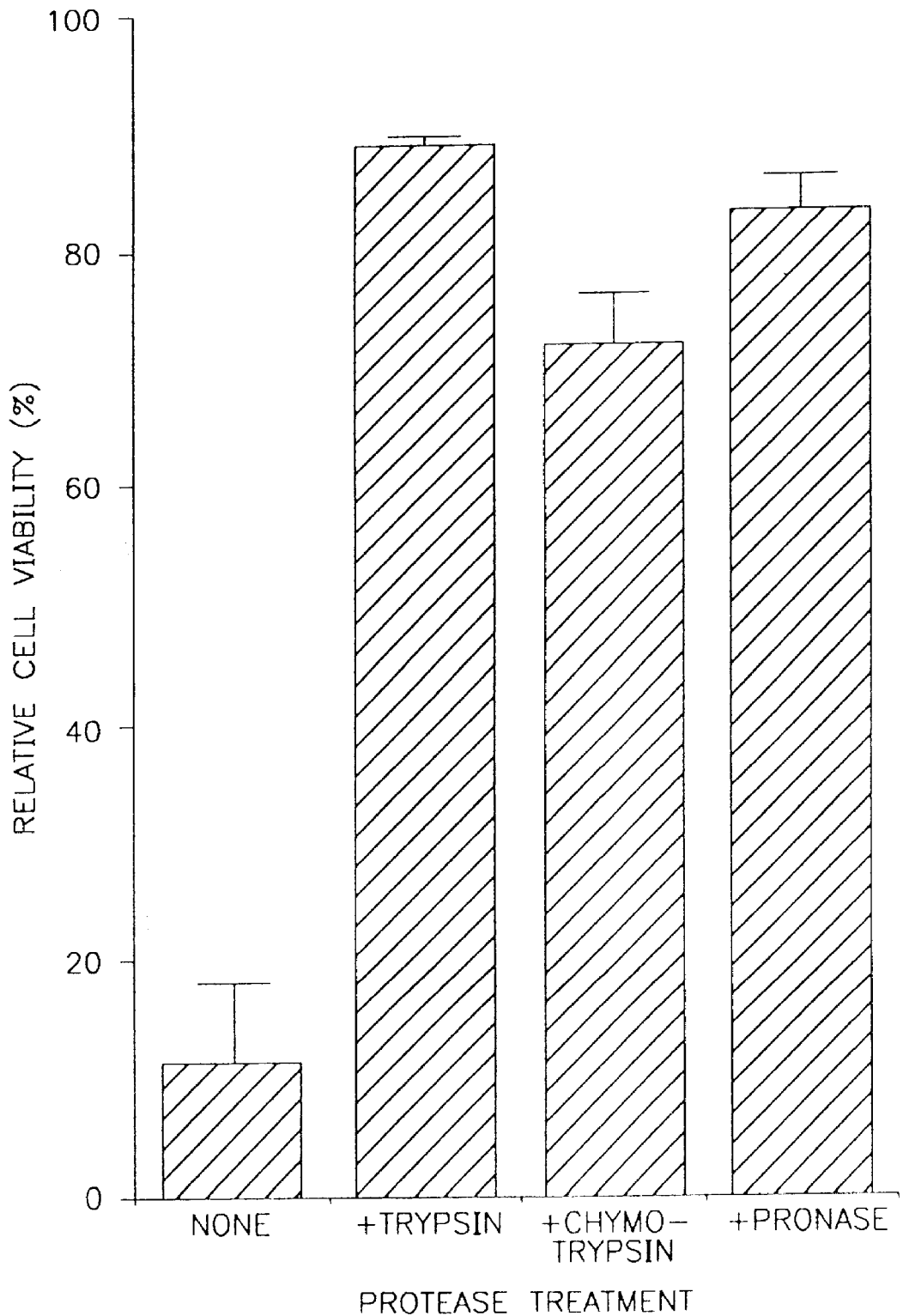
FIG. 6 shows the effect of pH (FIG. 6A) and organic solvents (FIG. 6B) on the biological activity of oncotoxin.
Figure 6A:
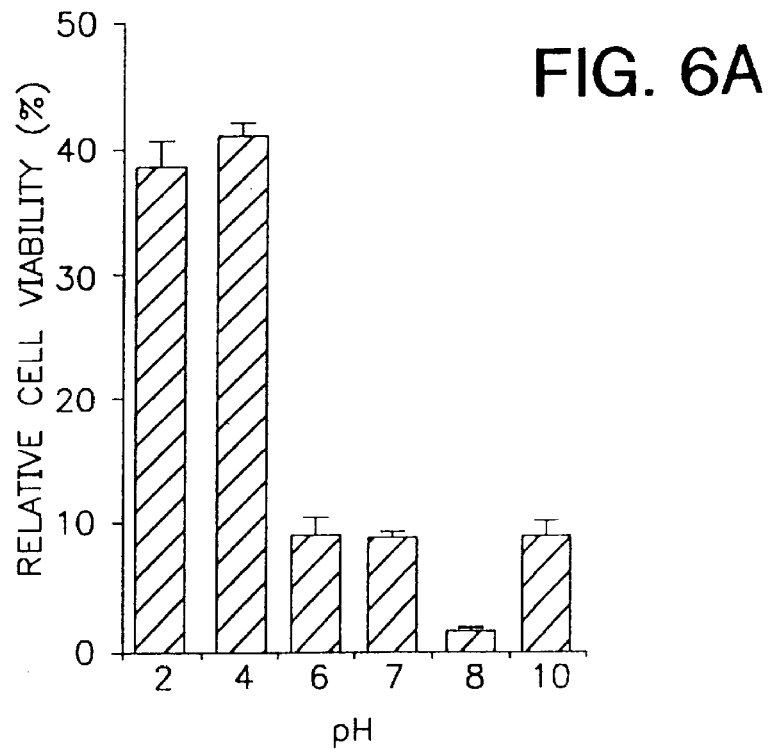
Figure 6B:
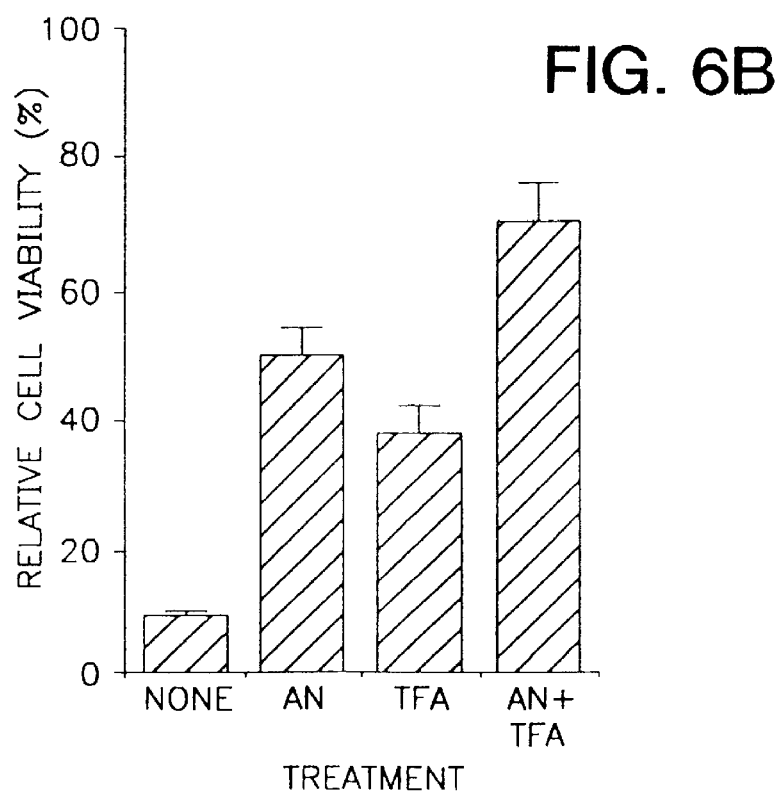

The treatment of oncotoxin to various proteases viz; trypsin, chymotrypsin and pronase (10%, w/w) for 24 hours abolished the activity of the protein (FIG. 5). These results indicate that the biological activity resides in full length protein. Besides proteases, the activity of oncotoxin was also found to be sensitive to acidic conditions. Although not completely, a significant amount of the activity was destroyed on exposure of oncotoxin to pH 2 (FIG. 6A). The oncotoxin activity was also found to be sensitive to treatment with trifluoroacetic acid (0.1%) or with acetonitrile (50%) (FIG. 6B.). The activity, however, was resistant to treatment with dithiothreiotol (1 mM for 2 hours) or exposure to 100° C. temperature for 30 minutes (data not shown).

EXAMPLE 15
Biological characterization of oncotoxin

Figure 7:
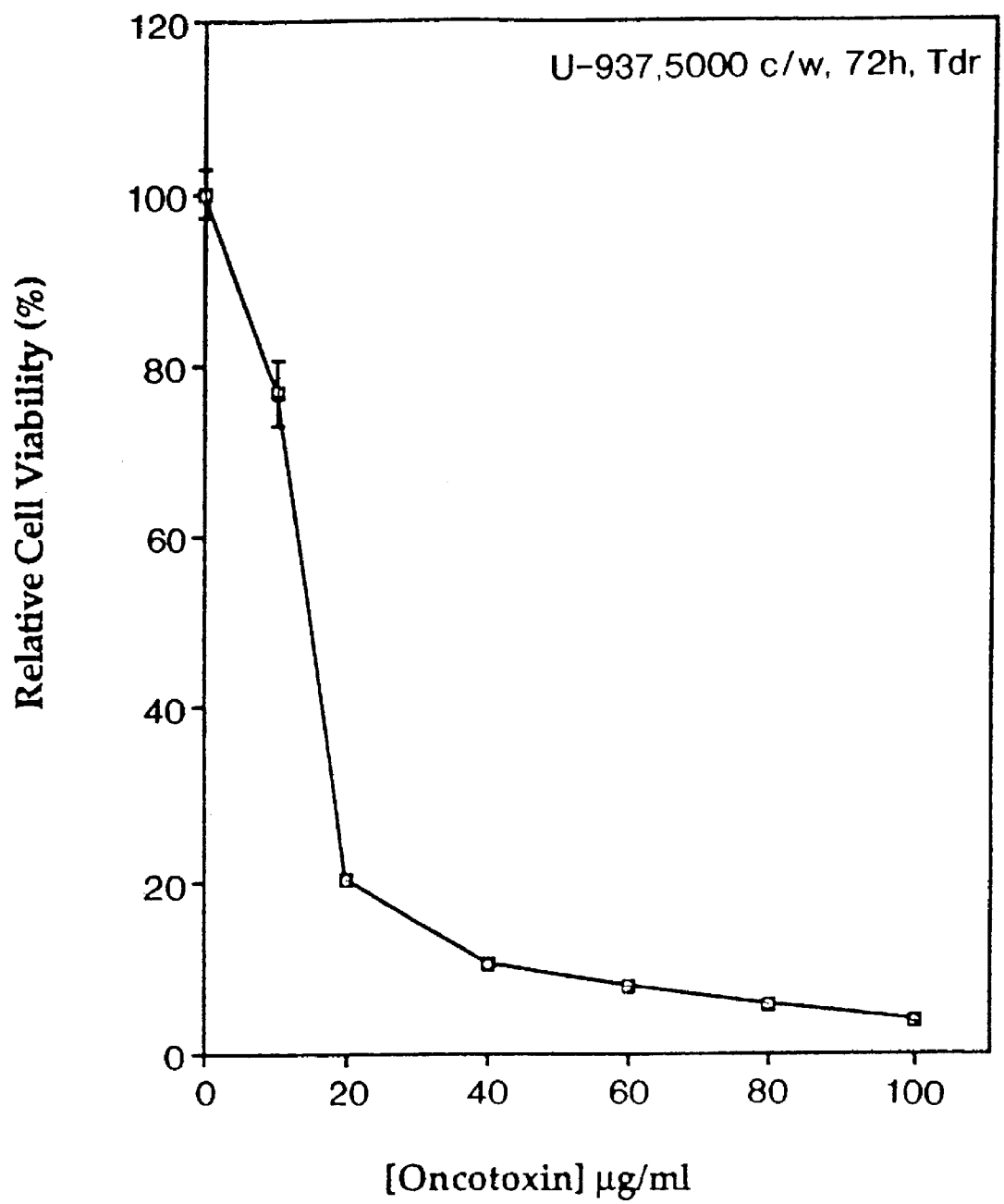
FIG. 7 shows the bioassay for oncotoxin. $5 \times 10^3$ cells (0.2 ml) in 96-well plates were incubated with oncotoxin at 37° C. for 72 hours and then the cell viability was determined by tritiated thymidine incorporation as described below. All determinations were made in triplicate.
Figure 8:
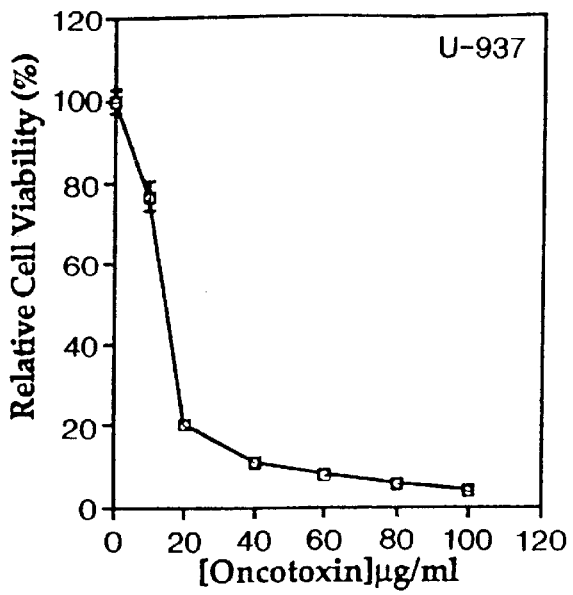
FIG. 8 shows the dose-dependent effect of oncotoxin on different myeloid cell lines.
Figure 8:
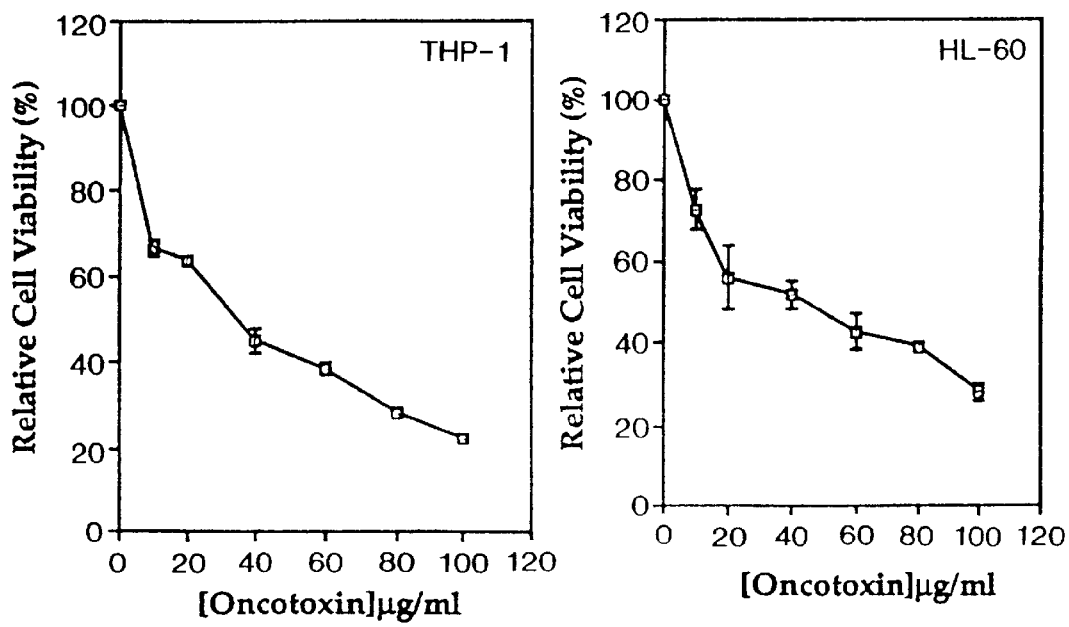
Figure 9A:
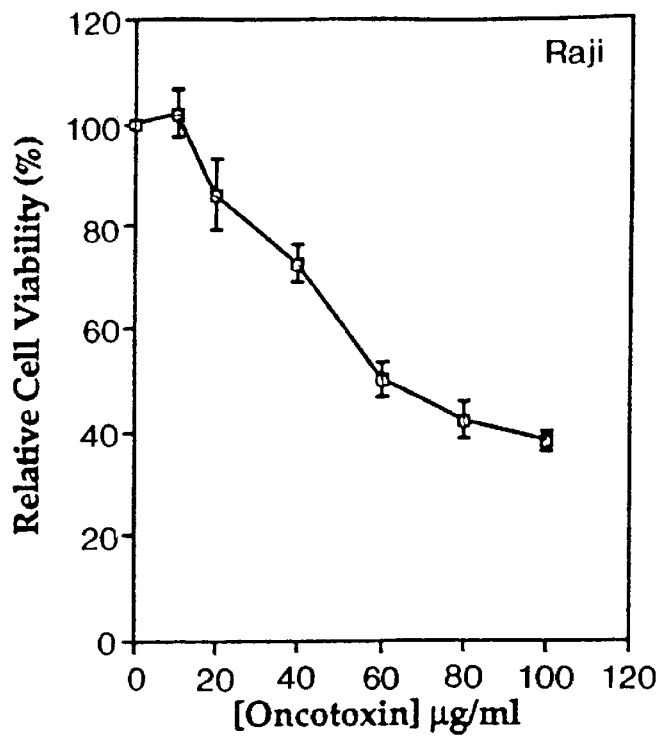
FIG. 9A shows the dose-dependent effect of oncotoxin on different lymphoid cell lines.
Figure 9A:
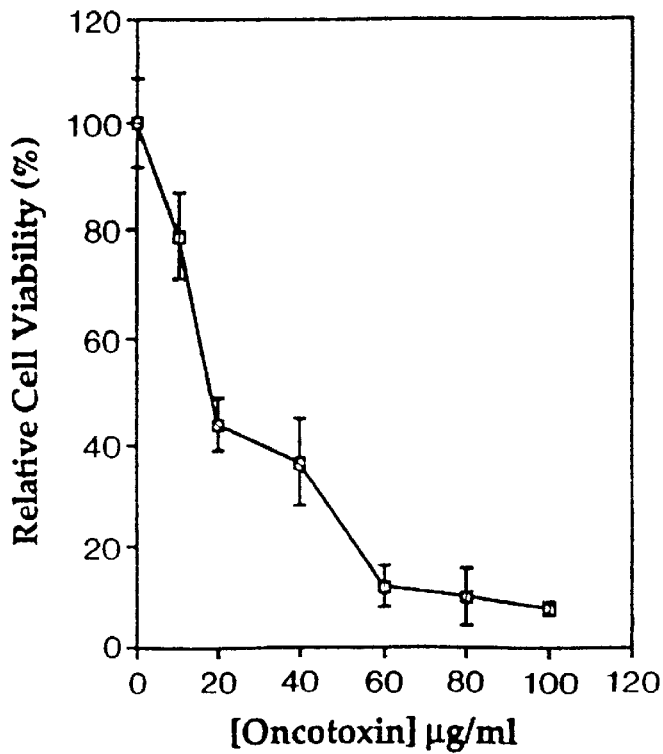
Figure 9B:
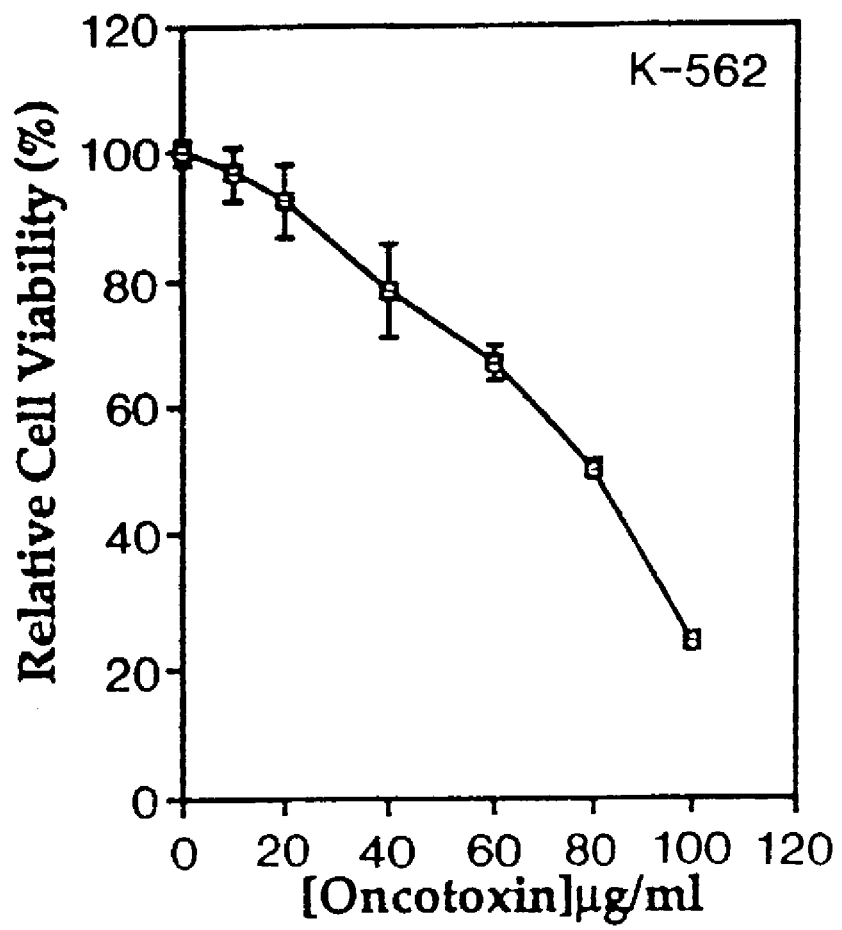
FIG. 9B shows the dose-dependent effect of oncotoxin on erythroblastoid cell line.
Figure 10:
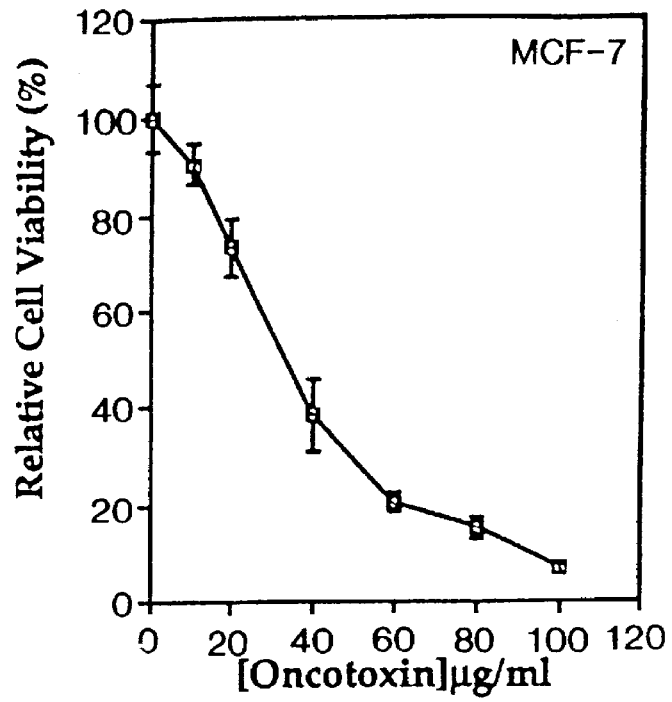
FIG. 10 shows the dose-dependent effect of oncotoxin on different breast tumor cell lines.
Figure 10:
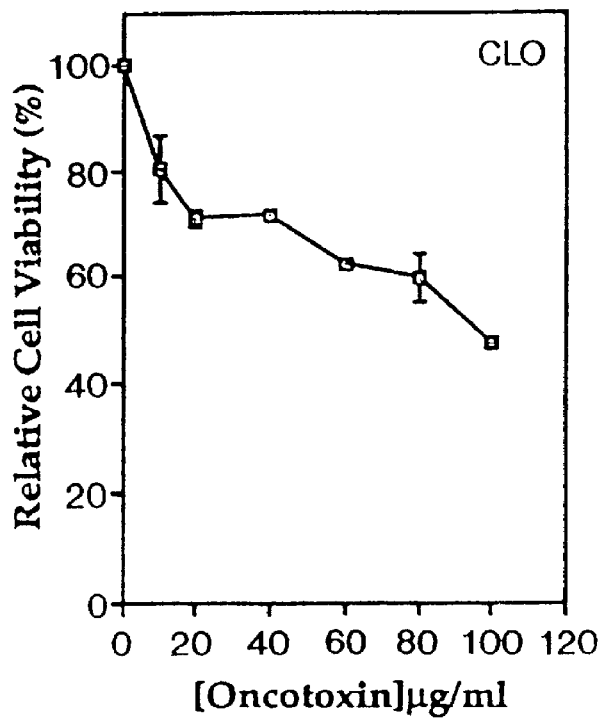
Figure 11:
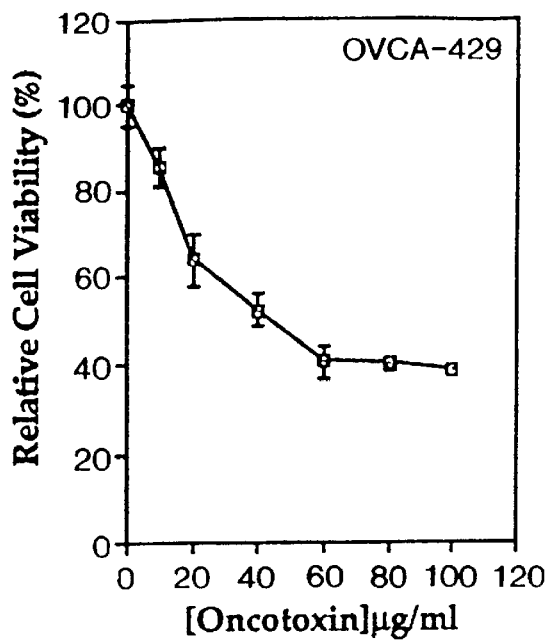
FIG. 11 shows the dose-dependent effect of oncotoxin on different ovarian tumor cell lines.
Figure 11:
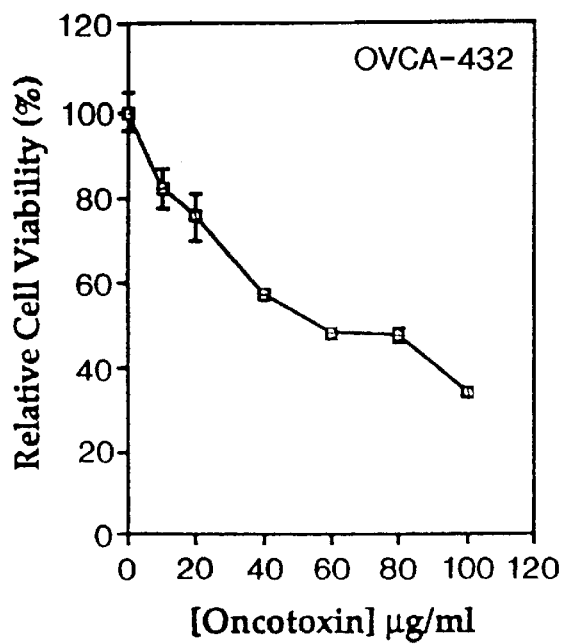
Figure 11:
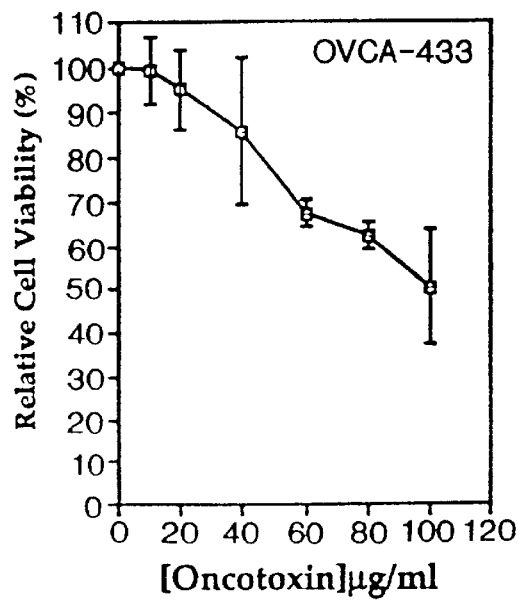
Figure 12:
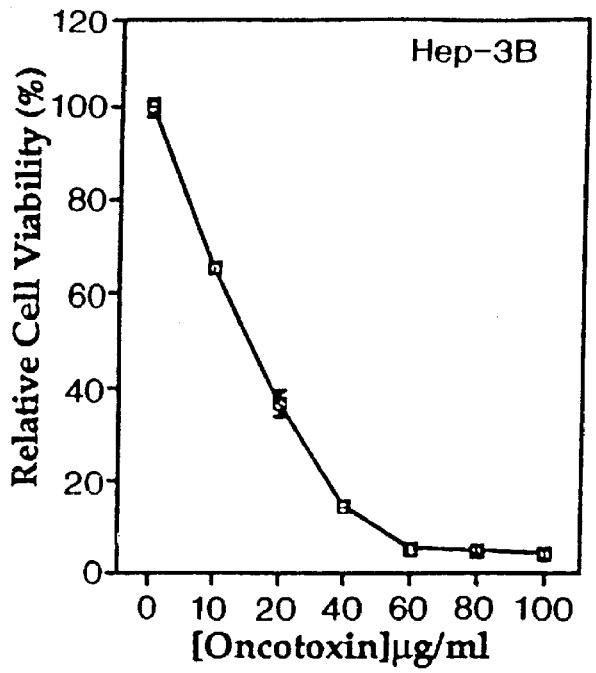
FIG. 12 shows the dose-dependent effect of oncotoxin on different hepatoma cell lines.
Figure 12:
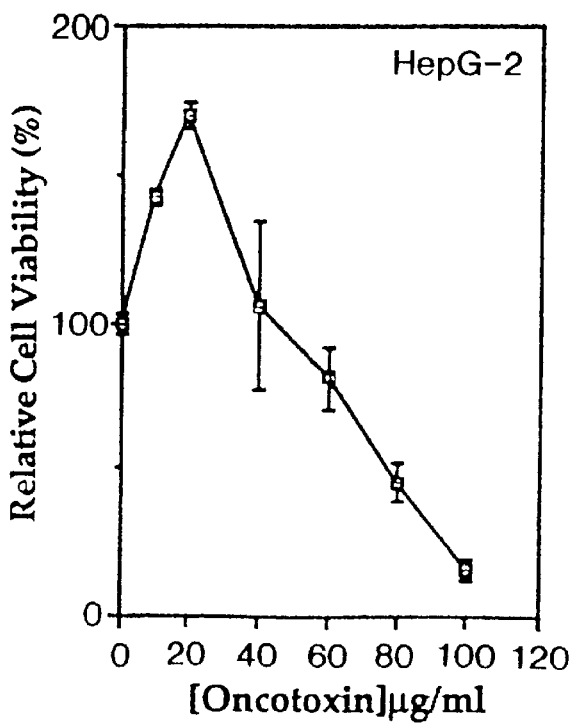
Figure 13:
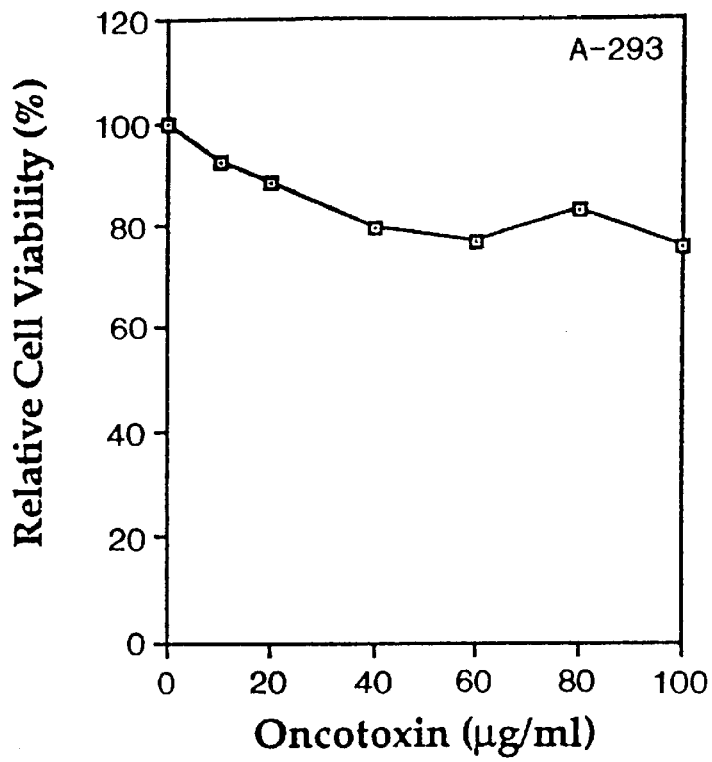
FIG. 13 shows the dose-dependent effect of oncotoxin on human embryonal kidney cell line.
Figure 14:
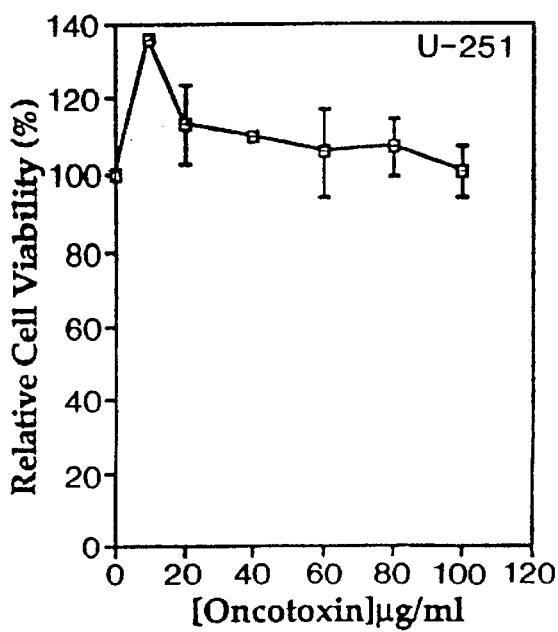
FIG. 14 shows the dose-dependent effect of oncotoxin on human glioblastoma cells.
Figure 15:
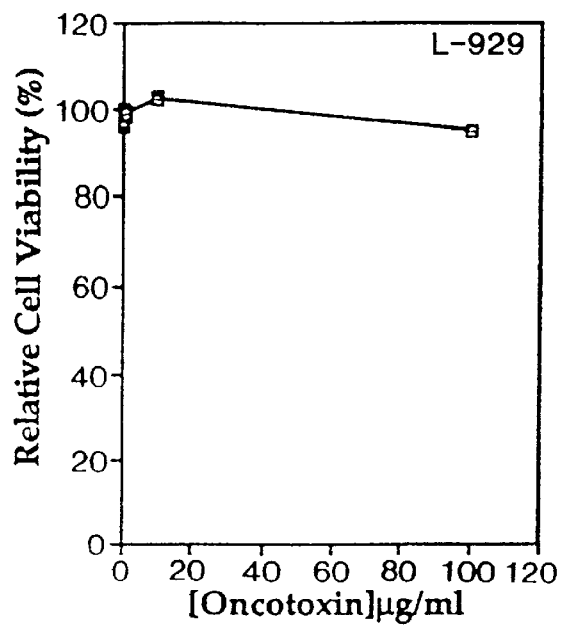
FIG. 15 shows the dose-dependent effect of oncotoxin on murine fibrosarcoma.

Treatment of U-937 cells with oncotoxin for 72 hours inhibited the growth of these cells as determined by thymidine incorporation (FIG. 7). A 50% inhibition was observed at 15 $\mu$g/ml concentration of oncotoxin. The effect of oncotoxin was also examined on several other type of cell lines. Oncotoxin was inhibitory for other myeloid cells (FIG. 8), lymphoid (both B and T) cells (FIG. 9A), erythroblastoid cells (FIG. 9B), breast tumor cells (FIG. 10), ovarian tumor cells (FIG. 11) and hepatoma (FIG. 12). Embryonal kidney cells were relatively resistant to oncotoxin (FIG. 13). Human glioblastoma cells and murine fibrosarcoma were found to be completely resistant to oncotoxin (FIG. 14 and FIG. 15). When analyzed for amount of oncotoxin required to induce 50% inhibition of cell growth, it varied significantly depending on the tumor cell type (Table I).

TABLE 1

Inhibition of growth of human tumor cell lines by Oncotoxin

| Cell Lines [Concentration] | 50% Growth Inhibitory (µg/ml) |
|---|---|
| Human Macrophage Tumor Cell Lines: | |
| Histiocytic Lymphoma (U-937) | 15 |
| Acute Monocytic Leukemia (THP-1) | 32 |
| Promyelocytic Leukemia (HL-60) | 52 |
| Human Hepatocellular Carcinoma: | |
| Hepatocellular Carcinoma (Hep 3B) | 15 |
| Hepatocellular Carcinoma (Hep G2) | 78 |
| Human T and B Lymphoma Cells: | |
| Acute T Cell Leukemia (Jurkart) | 25 |
| Burkitt B cell Lymphoma (Raji) | 63 |
| Human Breast Adenocarcinoma: | |
| Breast Adenocarcinoma (MCF-7) | 35 |
| Breast Adenocarcinoma (CLO) | 90 |
| Human Erythroleukemia: | |
| Chronic Myelogenous Leukemia (K-562) | 80 |
| Human Ovarian Adenocarcinoma: | |
| Ovarian Adenocarcinoma (OVCA-429) | 40 |
| Ovarian Adenocarcinoma (OVCA-432) | 50 |
| Ovarian Adenocarcinoma (OVCA-433) | 100 |
| Human Glioblastoma: | |
| Glioblastoma (U-251) | >100 |
| Others: | |
| Human transformed embryonal kidney (A-293) | >100 |
| Murine fibrosarcoma (L-929) | >100 |
| Normal Cells: | |
| Human foreskin diploid fibroblast | >100 |
| Human peripheral blood lymphocytes | >100 |

Cells (5 × $10^3$/0.1 ml) in 96-well plates were incubated for 72 h at 37° C. During last 6 hours, cells were pulsed with tritiated thymidine. All determinations were made in triplicate.

Figure 16:
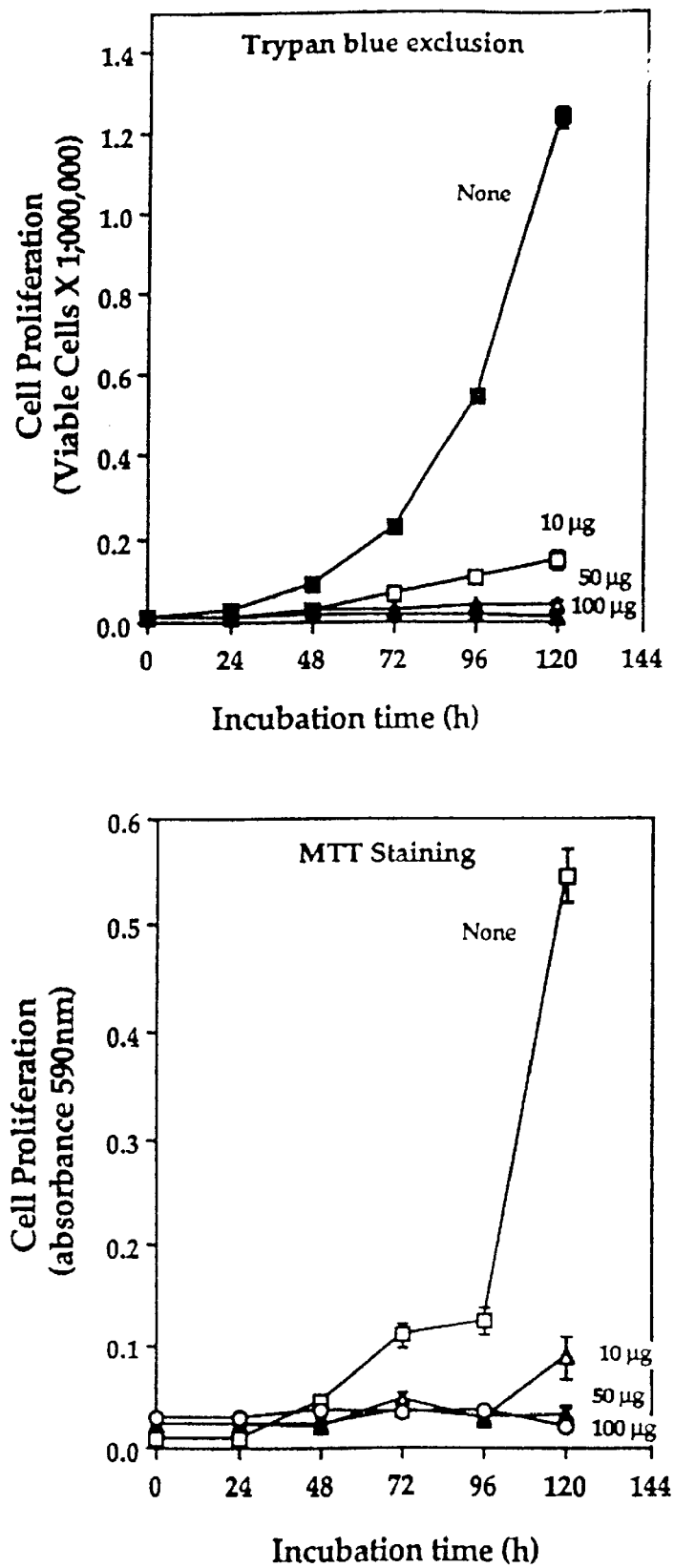
FIG. 16 shows the dose-dependent effect of oncotoxin on the growth of human histiocytic lymphoma U-937 cells by trypan blue exclusion method (FIG. 16A) and by MTT method (FIG. 16B).

Besides thymidine incorporation, cell growth was also monitored by trypan blue exclusion method and by staining of cells with MTT. The growth curve of U-937 cells by these two methods either with or without oncotoxin is shown in FIG. 16. These results also show complete inhibition of cell growth by oncotoxin.

Figure 17:
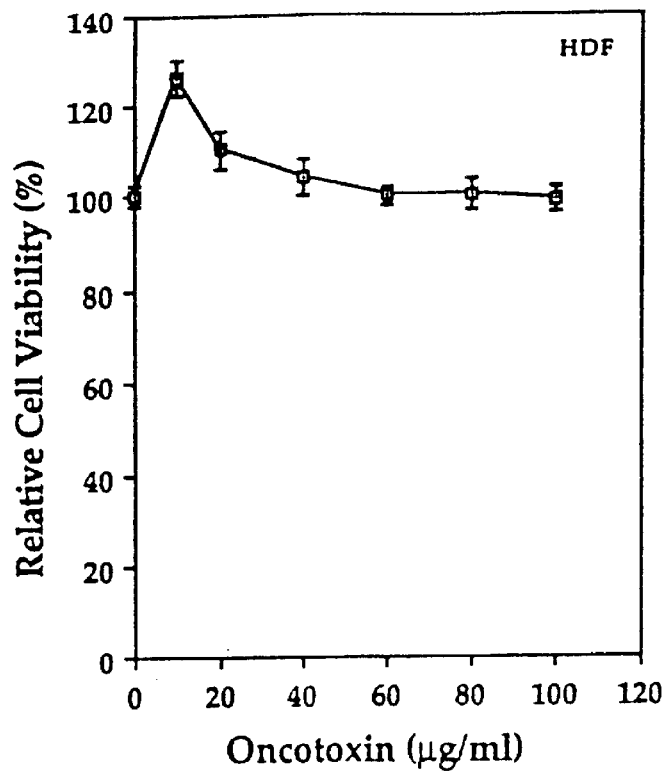
FIG. 17 shows the dose-dependent effect of oncotoxin on normal human diploid fibroblast (FIG. 17A) and normal human peripheral blood leukocytes (FIG. 17B).
Figure 17:
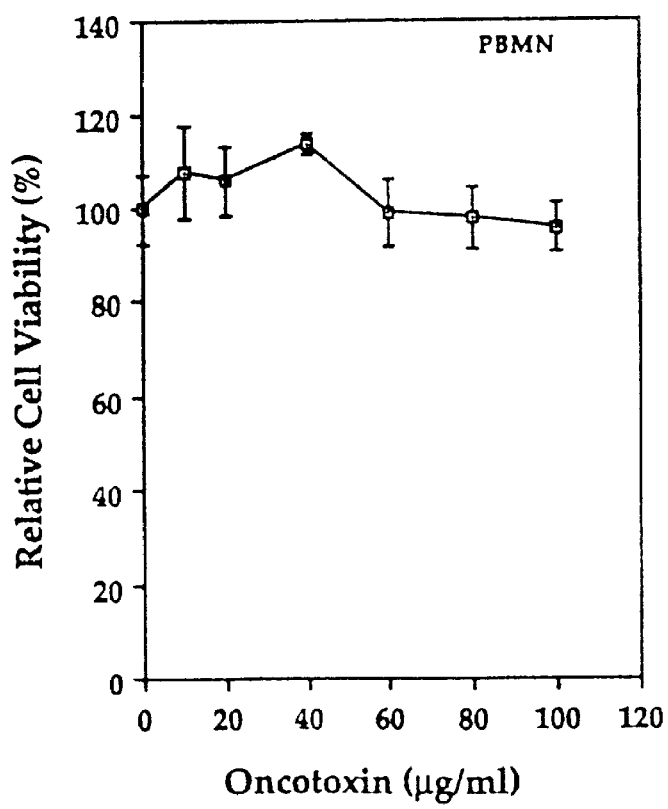

Besides tumor cells, several normal cells were tested for the sensitivity to oncotoxin (FIG. 17). Both normal fresh peripheral blood lymphocytes and human foreskin fibroblast were found to be resistant to oncotoxin even at 100 µg/ml concentration. These results demonstrate that oncotoxin is inhibitory only to tumor cells.

Figure 18:
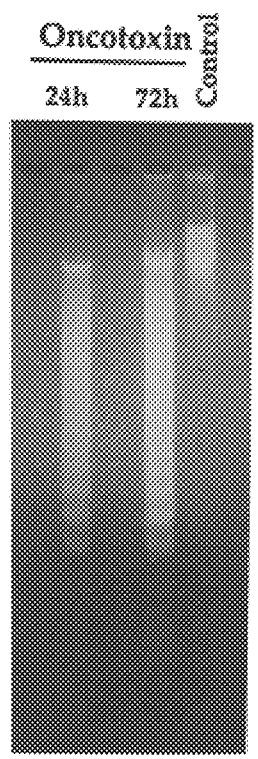
FIG. 18 shows the time-dependent effect of oncotoxin on DNA fragmentation in U-937 cells.

Morphologically there are two types of cell death, apoptosis which is characterized by DNA fragmenation, membrane disintegration and chromsome condensation, whereas necrotic cell death involves mitochondrial swelling. Treatment of U-937 cells with oncotoxin leads to DNA fragmentation (FIG. 18), thus indicating that cell death is through apoptosis.

Figure 19:
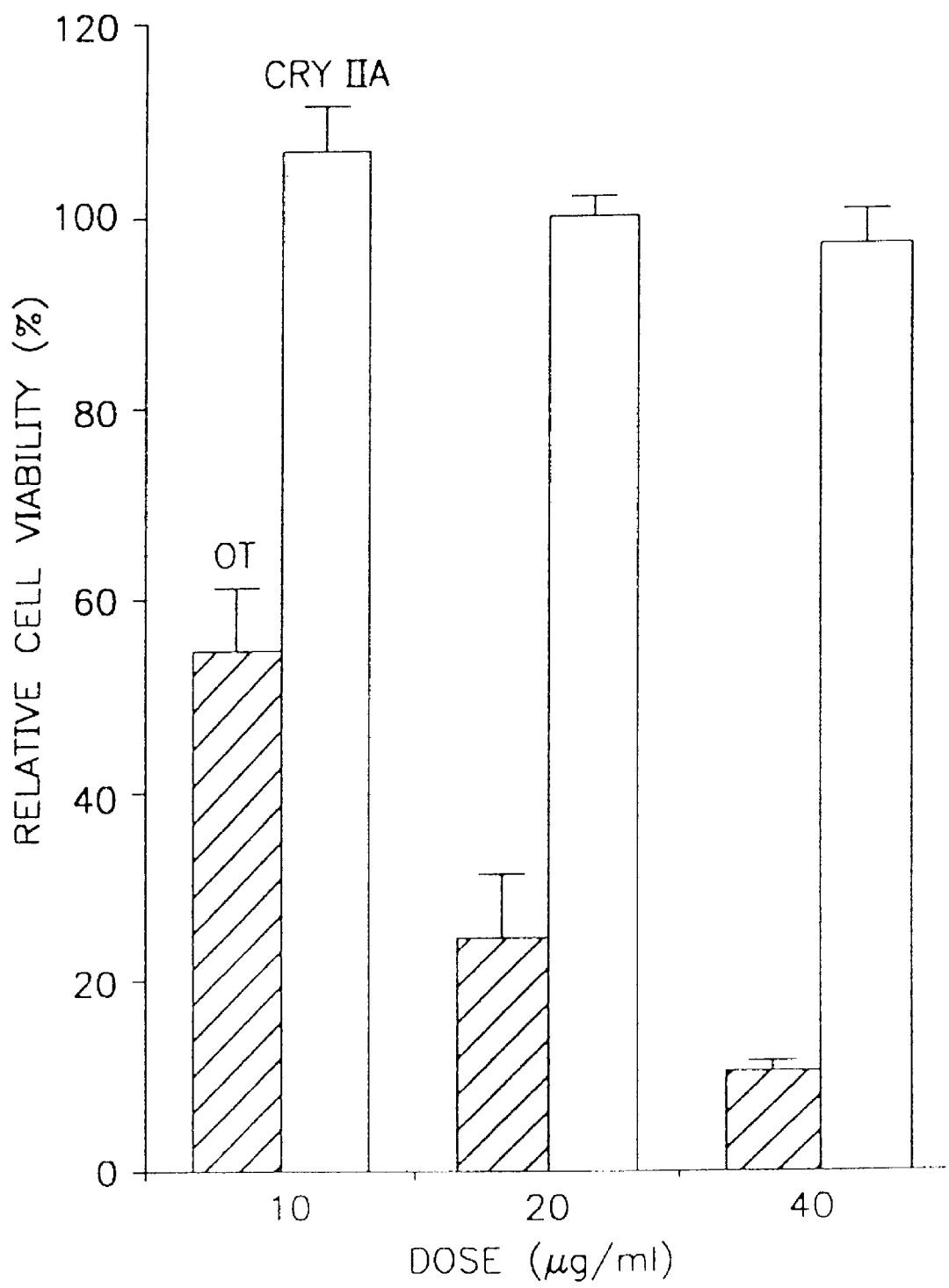
FIG. 19 shows the comparison of the oncotoxin activity with Cry IIA toxin from *Bacillus thuringiensis* kursataki.

The activity of oncotoxin was also compared with toxin isolated from another subspecies of *Bacillus thuringiensis*. The cDNA for toxin from *Bacillus thuringiensis* var.kurstaki has been cloned. Its predicted amino acid sequence is different from oncotoxin. *Bacillus thuringiensis* kursataki toxin made b y recombinant DNA method has a molecular mass of 66 kDa (called Cry IIA) (Donovan etal, 1988). The Cry IIA toxin had no effect in the bioassay (FIG. 19).

The present invention described here shows that *Bacillus thuringiensis* subspecies thuringiensis expresses a novel protein with an approximate molecular mass of 20 kDa. This protein, named oncotoxin, has a unique amino acid sequence and kills a wide variety of tumor cells but not normal cells, most likely through an apoptotic mechanism.

The amino acid sequence of oncotoxin derived from *Bacillus thuringiensis* thuringiensis is quite unique. A gene for a crystal protein Cry A4 from *Bacillus thuringiensis* thuringiensis (molecular size of 130 kDa) has been cloned (Brizzard and Whiteley, 1988). The sequence of oncotoxin is quite distinct from this protein. Also an acidic toxin with a molecular mass of 13 kDa has also been reported from *Bacillus thuringiensis* thuringiensis that exhibits both anti-tumor and insecticidal activity. This antitumor *Bacillus thuringiensis* thuringiensis protein is not oncotoxin due to the difference in molecular weight (13 kDa vs 20 kDa), and the presence of large number of acidic residues (42% Asp and Glu). Their isolation procedure also differed from that used herein in that their active fraction eluted at 0.27M NaCl on DEAE cellulose (oncotoxin elutes at 0.05M NaCl), and it did not involve a trypsin digestion step. This acidic toxin also lacked sulfur-containing amino acid residues and had a crystalline morphology. The amino acid sequence of the 13 kDa *Bacillus thuringiensis* thuringiensis has not been reported.

Another protein reported from *Bacillus thuringiensis* thuringiensis is a protoxin that is proteolytically activated by trypsin to release a toxin of molecular weight of 70,000 which is further degraded to a second one with a molecular weight of 55,000 (Huber-Lukac et al., 1983). This toxin is inactivated by heat and b y alkylation suggesting the role of specific confirmation and the sufhydryl groups. In contrast, oncotoxin is 20 kDa in size and is stable to both heat (100° C. for 30 minutes) and to reducing conditions. The toxin from *Bacillus thuringiensis* kursataki requires highly alkaline conditions for full expression of biological activity (Gringorten et al., 1992) and this feature is also different from oncotoxin. Moreover, *Bacillus thuringiensis* kursataki protein has not been shown to display antitumor activity. This is consistent with the observation as reported here with recombinant *Bacillus thuringiensis* kursataki toxin. Another protein derived from *Bacillus thuringiensis* israeliensis with a molecular size of 20 kDa promotes crystal formation of CytA protein (27.3 kDa) and this leads to inhibition of CytA toxicity (Wu and Federici, 1993).

Most crystal proteins from different subspecies of *Bacillus thuringiensis* contain two domain structures, an amino terminal half with α-helical structure that has toxin activity and the carboxyl terminal half with alternate β-strand and coil structure, is important for the assembly and stability of the crystal structure (Convents et al, 1990). The crystal structure of the d-endotoxin (cry IIIA, 60–70 kDa) has revealed it consists of three domains, a seven helix bundle, a three sheet domain and a β sandwich (Li etal, 1991). It was suggested that helices are equipped for pore formation in the membrane and the sheet domain is responsible for receptor binding.

There is very little known about the cytotoxic activity against tumor cells of the proteins derived from *Bacillus thuringiensis*. It has been shown that *Bacillus thuringiensis* israeliensis toxin of 25 kDa in size is by itself cytotoxic to murine tumor cells and it potentiates the cytotoxic effects of certain antitumor agents in vitro and in vivo (Thomas & Ellar, 1983; Yokoyama etal, 1988; Yokoyama et al, 1991). Among various chemotherapeutic agents, the highest synergy was observed with bleomycin. The protein derived from *Bacillus thuringiensis* thuringiensis has also been shown to be cytotoxic to murine tumor cells in vivo (Prasad and Shethna, 1973, 1974).

The mechanism by which *Bacillus thuringiensis* -derived proteins kill tumor cells is not known but it has been shown that *Bacillus thuringiensis* israeliensis-derived toxin binds specific plasma membrane lipids, causes a detergent-like rearrangment of the lipids leading to disruption of membrane integrity and eventual lysis (Thomas and Ellar, 1983). In insect cells the toxin inhibits (Na, K)-ATPase (English et al., 1986). Whether oncotoxin kills such a wide variety of cells by a similar mechanism is not clear. Oncotoxin induces DNA fragmentation in cells which is one of the hallmarks of apoptotic mechanism of cell death. Moreover, oncotoxin was found to be not toxic to normal cells. Not all the tumor cells, however, were found to be sensitive to oncotoxin.

The following references were cited herein:

Ang, B. J. et al., 1978. Purification of the protein crystal from *Bacillus thuringiensis* by zonal gradient centrifugation. Appl. Environ. Microbiol. 36: 625–626.

Adang, M. J. et al., 1985. Characterized full-length and truncated plasmid clones of the crystal protein of *Bacillus thuringiensis* subsp. kurstaki HD-73 and their toxicity to *Manduca sexta*. Gene, 36: 289–300.

Brizzard, B. L. et al., 1988. Nucleotide sequence of an addittional crystal protein gene cloned from *Bacillus thuringiensis* subsp.thuringiensis. Nucleic Acids Res., 16 (6): 2723–2724.

Bosch, D., et al., 1994. Recombinant *Bacillus thuringiensis* crystal proteins with new properties: Possibilities for resistance Management. Bio/Technology,12: 915–918.

Cheung, P. et al., 1985. Separation of three biologically distinct activities from the parasporal crystal of *Bacillus thuringiensis* var.israelensis. Current Microbiology 12: 121–126.

Choma, C. T., et al., 1990. Unusual proteolysis of the protoxin and toxin from *Bacillus thuringiensis*. Structural implications. Eur. J. Biochem. 189: 523–527.

Convents, D., et al., 1990. The *Bacillus thuringiensis* d-Endotoxin. J. Biol. Chem., 265 : 1369–1375.

Convents, D., et al., and Lauwereys, M. 1991. Two structural domains as a general fold of the toxic fragment of the *Bacillus thuringiensis* d-endotoxins. Eur. J. Biochem. 195: 631–635.

Donovan W.P., et al., (1988) Amino acid sequence and entomocidal activity of the P2 crystal protein: an insect toxin from *Bacillus thuringiensis* var. kurstaki. J. Biol. Chem. 263: 561–567

English, L. et al., 1986. Delta endotoxin is a potent inhibitor of the (Na, K)- ATPase. J. Biol. Chem., 261: 1170–1173.

Green, M., et al., 1990. Public health implications of the microbial pesticide *Bacillus thuringiensis:* An epidemiological study, Oregon, 1985–86. American J. Public Health, 80 : 848–852.

Gringorten, et al., 1992. Suppression of *Bacillus thuringiensis* α-endotoxin activity by low alkaline pH. J. Invertebrate Pathol., 60:47–52.

Galjart, N. et al., 1987. Plasmid location, cloning, and sequence analysis of the gene encoding a 27.3 Kilodalton cytolytic protein from *Bacillus thuringiensis* subsp. morrisoni (PG-14). Current Microbiol., 16: 171–177.

Geiser, M., et al., 1986. The hypervariable region in the genes coding for entomopathogenic crystal proteins of *Bacillus thuringiensis:* nucleotide sequence of the kurdh 1gene of subsp. kurstaki HD1. Gene, 48: 109–118.

Hofte, H. et al., 1989. Insecticidal crystal proteins of *Bacillus thuringiensis*. Microbiological Reviews, 53 (2): 242–255.

Huber-Lukac, M., et al., 1983. Specificities of monoclonal antibodies against the activated d-endotoxin of *Bacillus thuringiensis* var. thuringiensis. Infect. and Immun., 40 : 608–612.

Higuchi, M. et al., 1992. Modulation of two forms of tumor necrosis factor receptors and their cellular response by soluble receptors and their monoclonal antibodies. J. Biol. Chem. 267: 20892.

Hansen, M. B., et al., 1989. Re-examination and further development of a precise and rapid dye method for measuring cell growth/cell kill. J. Immunol. Methods 119: 203.

Koni, P. A. et al., 1993. Cloning and characterization of a novel *Bacillus thuringiensis* cytolytic delta-endotoxin. J. Mol. Biol., *: 319–327.

Luthy, P., et al., 1982. Physiology of the delta endotoxin of *Bacillus thuringiensis* including the ultrastructure and histopathological studies. in Basic Biology of Microbial Larvicides of Vectors of Human Diseases; Proc. of Consultation Convened in Geneva, pp29–36

Lereclus, D. et al., 1995. Overproduction of encapsulated insecticidal crystal proteins in a *Bacillus thuringiensis* spo OA mutant. Bio/Technology, 13: 67–71.

Li, J., et al., 1991. Crystal structure of insecticidal d-endotoxin from *Bacillus thuringiensis* at 2.5 Å resolution. Nature. 353: 815–821

Montgomery R. et al., (1981) in Oligopeptides and Proteins in Antitumor Compounds of Natural Origin (Aszalos A. Ed.) CRC Press, Boca Raton, Fla.

Mummigatti, S. G. et al., 1990. Influence of media composition on the production of d-endotoxin by *Bacillus thuringiensis* var.thuringiensis. J. Invertebrate Pathol., 55: 147–151.

Ogiwara K., et al., (1992) Processing of d-endotoxin from *Bacillus thuringiensis* subsp. kurstaki HD-1 and HD-73 by gut juices of various insect larvae. J. Invertebrate Pathol. 60: 121–126

Prasad, S. et al., 1973. Inhibitory activity of the parasporal crystal of *Bacillus thuringiensis* var.thuringiensis. on Yoshida ascites sarcoma. Current Sci. 42: 568–570

Prasad, S. et al., 1974. Purification crystalization and partial characterization of the antitumor and insecticidal protein subunit from the d-endotoxin of *Bacillus thuringiensis* var.thuringiensis. Biochim. Biophys. Acta. 3663: 558–566.

Prasad, S. et al., 1975. Enhancement of immune response by the proteinaceous crystal of *Bacillus thuringiensis* var. thuringiensis. Biochem. Biophys. Res. Commun., 62: 517–523.

Prasad, S. et al., 1976a. Antitumor immunity against Yoshida ascites sarcoma after treatment with the proteinaceous crystal of *Bacillus thuringiensis* thuringiensis . Antimicrobial Agents & Chemo., 14: 285–288.

Prasad, S. et al., 1976b. Mode of action of a purified antitumor protein from the proteinaceous crystal of *Bacillus thuringiensis* thuringiensis on Yoshida ascites sarcoma cells. Antimicrobial Agents & Chemotherapy, 10 (2): 293–298.

Prasad, S. et al., 1976c. Biochemistry and biological activities of the proteinaceous crystal of *Bacillus thuringiensis*. Biochemical Rev., 47: 70–76.

Schnepf, H. et al., 1985. The amino acid sequence of a crystal protein from *Bacillus thuringiensis* deduced from DNA base sequence. The Journal of Biological Chemistry, 260 (10): 6264–6272.

Thomas, W. et al., 1983. *Bacillus thuringiensis* var. israelensis crystal d-endotoxin: effects on insect and mammalian cells in vitro and in vivo. J. Cell Sci., 60: 181–197.

Vandre D. et al., (1982) Largomycin: Preparation properties and structure. Biochemistry 21: 5089–5096

Waalwijk, C., et al.,. 1985. Molecular cloning and the nucleotide sequence of the $M_r$ 28 000 crystal protein gene of *Bacillus thuringiensis* subsp.israelensis. Nucleic Acids Res., 13: 8207–8217.

Ward, E. et al., 1986. *Bacillus thuringiensis* var. israelensis d-endotoxin nucleotide sequence and characterization of the transcripts in *Bacillus thuringiensis* and *Escherichia coli*. J. Mol. Biol., 191: 1–11.

Ward, E. et al., 1986. *Bacillus thuringiensis* var. israelensis α-endotoxin. Cloning and expression of the toxin in sporogenic and asporogenic strains of *Bacillus subtilis*. J. Mol. Biol., 191: 13–22.

Wu, D. and Chang, F. N. 1985. Synergism in mosquitocidal activity of 26 and 65 KDa proteins from *Bacillus thuringiensis* subsp. israelensis crystal FEBS Lett,190: 232–236.

Wu, Dong and Federici, B. A. 1993. A 20-Kilodalton protein preserves cell viability and promotes cytA crystal formation during sporulation in *Bacillus thuringiensis*. J. Bacteriol., 175: 5276–5280.

Waring M. J. and Ponder B. A. J. (eds.) (1992). The Search for New Anticancer Drugs. Kluwer Acad. Press, Boston.

Yamamoto, T. et al., 1981. Isolation of a protein from the parasporal crystal of *Bacillus thuringiensis* var. kurstaki: toxic to the mosquito larva, *Aedes taeniorhynchus*. BBRC. 103 : 414–421.

Yamamoto, T. and Ilzuka, T. 1983. Two types of entomocidal toxins in the parasporal crystals of *Bacillus thuringiensis* kurstaki. Arch. Biochem.Biophys.227: 233–241.

Yokoyama, Y., et al., 1988. Potentiation of the cytotoxic activity of anti-cancer drugs in cultured L1210 cells by *Bacillus thuringiensis* subsp.sraelensis toxin. Chem. Pharm. Bull.,36:4499–4504.

Yokoyama, Y. et al., 1991. Potentiation of antitumor activity of bleomycin towards solid tumors in mice by *Bacillus thuringiensis* subsp. israelensis toxin. Anticancer Res., 11: 1625–1628.

Yokoyama, Y. et al., 1992. Hyperthermic potentiation of bleomycin cytotoxicity in the presence of *Bacillus thuringiensis* subsp. israelensis d-endotoxin. Anticancer Res., 12: 1079–1082.

Yokoyama, Y. and Kohda, K. 1994. Enhanced cytotoxicity caused by increased DNA strand breakage resulting from synergistic potentiation of bleomycin with *Bacillus thuringiensis* subsp. sraelensis d-endotoxin. Anticancer Res., 14: 838–840.

Yan, X. and McCarty, W. J. 1991. Chemical modification of *Bacillus thuringiensis* subsp.thuringiensis (HD-524) trypsin-activated endotoxin: implication of tyrosine residues in lepidopteran cell lysis. J. Invertebrate Pathol., 57: 101–108.

Yoshisue, H., et al., 1993. Identification of a promoter for the crystal protein-encoding gene cry IVB from *Bacillus thuringiensis* subsp.israelensis. Gene, 137: 247–251.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated and purified protein derived from *Bacillus thuringiensis* subspecies thuringiensis, having a molecular weight of approximately 20 kDa as determined by SDS-PAGE, said protein having the partial amino acid sequence shown in SEQ ID No. 1, and wherein said protein displays cytotoxic effects against tumor cells.

2. The protein of claim 1, wherein said protein is sensitive to proteases and acidic conditions and wherein said cytotoxic effects are resistant to treatment with dithiothreiotol or exposure to 100° C. temperature.

3. The protein of claim 1, wherein said protein is cytotoxic to U-937 cells, myeloid cells, B lymphoid cells, T lymphoid cells, erythroblastoid cells, breast tumor cells, ovarian tumor cells and hepatoma cells.

4. The protein of claim 1, wherein said cytotoxic effects are blocked by an antibody directed against the protein.

5. The protein of claim 1, wherein said protein is not cytotoxic to normal human peripheral blood lymphocytes and human foreskin fibroblast cells.

6. A pharmaceutical composition, comprising the protein of claim 1 and a pharmaceutically acceptable carrier.

7. A method of treating a neoplastic cell comprising administering a therapeutically effective dose of the composition of claim 6 to said cell.

8. The method of claim 7, wherein said neoplastic cell is selected from the group consisting of myeloid cells, B lymphoid cells, T lymphoid cells, erythroblastoid cells, breast tumor cells, ovarian tumor cells and hepatoma cells.

9. The method of claim 7, wherein said neoplastic cell occurs in a human or animal.

10. The method of claim 7, wherein said composition retards recurrence of a neoplastic condition.

11. The method of treating of claim 7, wherein said neoplastic cell is in vitro.

* * * * *

UNITED STATES PATENT AND TRADEMARK OFFICE
CERTIFICATE OF CORRECTION

PATENT NO. : 5,824,636
DATED : October 20, 1998
INVENTOR(S) : Bharat B. Aggarwal, et al It is certified that error appears in the above-identified patent and that said Letters Patent is hereby corrected as shown below:

Column 1,
Line 34, "et al" should read -- et al.,--.
Line 42, "etal" should read -- et al.,--.
Line 49, please italicize the words "israeliensis" and "kyushunsis".
Line 49, "kursataki" should read -- *kurstaki* --.
Line 51 please italicize the word "israeliensis."
Line 53, please italicize the word "morrisoni".
Line 54, "kurastaki" should read -- kurstaki --.
Line 61, please italicize the word "in vivo".
Line 62, please italicize the word "israeliensis".
Line 64, please italicize the word "thuringiensis".

Column 2,
Line 12, please italicize the word "thuringiensis".
Line 54, "lead" should read -- leads --.
Line 59, please insert the word -- a -- between the words "against" and "wide".

Column 4,
Line 12, "kursataki" should read -- *kurstaki* --.
Line 44, please italicize the word "in vivo".

Column 5,
Line 28, please italicize the word "in vivo".
Line 57, please italicize the word "kurstaki".
Line 58, "etal," should read -- et al.,--.

Column 6,
Line 28, please italicize the word "in vivo".
Line 30, "University of" should read -- Universidadde --.
Line 52, "25 000" should read -- 25,000 --.

Column 8,
Line 40, "10, 000" should read -- 10,000 --.

UNITED STATES PATENT AND TRADEMARK OFFICE
CERTIFICATE OF CORRECTION

PATENT NO.   : 5,824,636
DATED        : October 20, 1998
INVENTOR(S)  : Bharat B. Aggarwal, et al It is certified that error appears in the above-identified patent and that said Letters Patent is hereby corrected as shown below:

Column 10,
Line 37, "b y" should read -- by --.
Lines 41, 44 and 47, "kursataki" should read --*kurstaki* --.
Line 48, please italicize the word "isaeliensis".
Line 57, please insert a comma after the word "et al."
Line 60, "etal," should read -- et al.,--.
Line 67, please italicize the word "israeliensis".

Column 11,
Line 2, please italicize the words "in vivo" and "in vitro".
Line 6, please italicize the word "thuringiensis".
Line 11, italicize the word "israeliensis".
Line 31, "addittional" should be -- additional --.
Line 32, please italicize the word "thuringiensis".
Line 39, please italicize the word "israeliensis".
Line 52, please italicize the word "kurstaki".
Line 66-67, please italicize the word "morrisoni".

Column 12,
Line 4, please italicize the word "kurstaki".
Line 9, please italicize the word "thuringiensis'.
Line 40, please italicize the word "kurstaki".
Lines 44, 49, 53 and 57, please italicize the word "thuringiensis".

Column 13,
Lines 3-4, 10, 12-13, 16-17, and 22, please italicize the word "israelensis".
Lines 32 and 37, please italicize the word kurstaki".

UNITED STATES PATENT AND TRADEMARK OFFICE
CERTIFICATE OF CORRECTION

PATENT NO. : 5,824,636
DATED : October 20, 1998
INVENTOR(S) : Bharat B. Aggarwal, et al.

It is certified that error appears in the above-identified patent and that said Letters Patent is hereby corrected as shown below:

<u>Column 14,</u>
Line 1, "subsp.sraelensis" should read-- subsp. *israelensis* --.
Line 5, please italicize the word "israelensis".
Line 14, "sraelensis" should read -- israelensis --.
Line 17, please italicize the word "thuringiensis".

Signed and Sealed this

Fourteenth Day of August, 2001

*Attest:*

*Attesting Officer*

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 20
        ( B ) TYPE: amino acid
        ( C ) STRANDEDNESS:
        ( D ) TOPOLOGY: linear ( i i ) MOLECULE TYPE:
        ( A ) DESCRIPTION: protein ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:1:

Pro Ser Thr Val Val Asn Val Ser Asn Leu Lys Pro Gly Asp Thr Ile
1               5                   10                  15
Glu Lys Glu Phe
        20